United States Patent [19]

Garcia

[11] Patent Number: 4,516,584

[45] Date of Patent: May 14, 1985

[54] SUTURE COLLAR

[75] Inventor: Leonard M. Garcia, Severna Park, Md.

[73] Assignee: Cordis Corporation, Miami, Fla.

[21] Appl. No.: 456,532

[22] Filed: Jan. 7, 1983

[51] Int. Cl.³ .............................................. A61N 1/04
[52] U.S. Cl. .................................... 128/785; 128/786; 128/419 P
[58] Field of Search ................................ 604/174–175, 604/178; 128/419 P, 785, 784, 786, 642

[56] References Cited

U.S. PATENT DOCUMENTS

| | | | |
|---|---|---|---|
| 2,127,903 | 8/1938 | Bowen | 128/335.5 |
| 3,176,690 | 4/1965 | H'Doubler | 128/348 |
| 3,730,187 | 5/1973 | Reynolds | 128/349 |
| 3,738,368 | 6/1973 | Avery et al. | 128/784 |
| 3,788,328 | 1/1974 | Alley et al. | 604/178 |
| 3,821,957 | 7/1974 | Riely et al. | 128/348 |
| 3,880,169 | 4/1975 | Starr et al. | 128/785 |
| 4,276,882 | 7/1981 | Dickhudt et al. | 128/784 |
| 4,287,891 | 9/1981 | Peters | 128/348 |
| 4,338,947 | 7/1982 | Williams | 128/785 |
| 4,437,475 | 3/1984 | White | 128/334 R |

Primary Examiner—Stephen C. Pellegrino
Assistant Examiner—Gene B. Kartchner
Attorney, Agent, or Firm—Henry W. Collins; Thomas R. Vigil

[57] ABSTRACT

The suture collar (20) is used with a pacing lead body (12), and comprises a generally cylindrical body having a throughbore (46) therethrough for receiving therethrough the pacing lead body 12, the cylindrical body (20) including a middle barrel portion (29) and tapering end portions (30 and 32), each of which taper from the barrel portion (28) to a sleeve end section (70 and 72). The barrel portion (28) is separated from the tapering end portions (30 and 32) by first and second suture receiving annular grooves (34 and 36), and the barrel portion has four slits (41–44) therein to facilitate squeezing of the barrel portion 28 around lead body (12) when sutures (24 and 26) are tied in the grooves.

The suture collar (20) of the type defined above is secured to a lead body (12) by the following method including the steps of: sliding the suture collar (20) on the lead body (12) to the place of entry of the lead body (12) into a vein after an electrode tip has been inserted into and properly located within a ventricle or atrium of a heart (14); tying sutures (24 and 26) to the underlying tissue or the ligated vein in the area of the annular grooves (34 and 36); and then securing the sutures (24 and 26) tightly around the collar (20) in each groove (34 or 36) so as to cause radial displacement of the barrel portion quarter sections (81–84) against the lead body (12).

10 Claims, 8 Drawing Figures

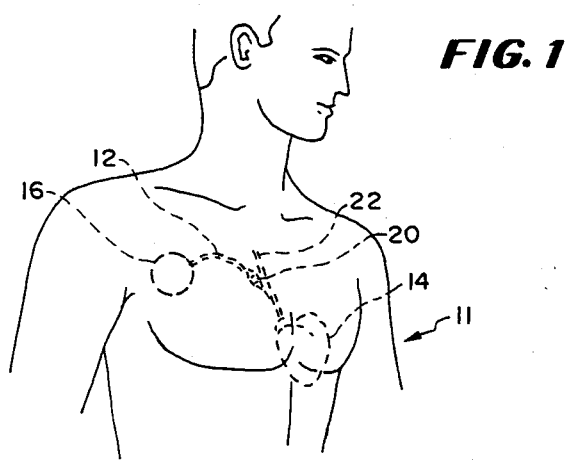

SUTURE COLLAR

FIELD OF THE INVENTION

The present invention relates to a suture collar or sleeve which is received over a lead body of a pacing lead and is utilized in fixing the lead to underlying tissue or to a ligated vein during the implanting of a lead electrode within a heart.

DESCRIPTION OF THE PRIOR ART

Heretofore in the implantation of a pacing lead, namely of the electrode at the distal end thereof in an atrium or ventricle of a heart, a surgeon makes an incision at the venous site of choice. Typically entry is made in the right or left cephalic vein or the right external jugular vein near the site chosen for a pocket for the so-called pacer or pacemaker containing a pulse generator. Then the tip electrode of the lead is inserted into the vein, and then into an atrium or ventricle of the heart and fixed in place. After determining that the electrode position is satisfactory, the lead is connected to a pacer also to be implanted.

Then a silicone elastomer suture sleeve that is movable on the lead is grasped at the tapered end and slid to a location where it is desired to fasten the lead to tissue or to the ligated vein. One or more sutures are first fastened to underlying tissue or to the ligated vein.

Examples of catheter tubing securing means of the type that are utilized for securing a lead body to tissue or a ligated vein are disclosed in the following U.S. Patents:

| U.S. PAT. NO. | PATENTEE |
|---|---|
| 3,176,690 | H'Doubler |
| 3,724,467 | Avery et al. |
| 3,730,187 | Reynolds |
| 3,821,957 | Riely et al. |
| 3,853,130 | Sheridan |
| 3,880,169 | Starr et al. |
| 4,287,891 | Peters |

In the Reynolds U.S. Pat. No. 3,730,187 there is disclosed a split collar which is C shaped in cross section and which has a plurality of sharp teeth or prongs that can grip the outer surface of a catheter when it is adjustably positioned in a desired place. A suture material is embedded within the collar and exits at the opening of the C in the C shaped collar.

In the Riely et al. U.S. Pat. No. 3,821,957 four slits are provided in a tubular body so that four arms can be folded out therefrom to form a retention slide for a catheter or tube.

In the H'Doubler U.S. Pat. No. 3,176,690 there is provided a catheter having tabs or flanges projecting therefrom which have openings therein for receiving a suture for securing to the skin of a patient.

In the Peters U.S. Pat. No. 4,287,891 there is illustrated a surgical safety holding device which is adapted to be fixed externally to the body of a patient and fitted with a body tube. The device is used for securing the body tube against displacement. The device includes two relatively rotatable tubular members telescoped together and defining a bore therein for receiving the body tube.

As will be described in greater detail hereinafter, the suture collar of the present invention provides a suture collar having a generally cylindrical body and a throughbore through the collar with radially extending slits in the body in the middle portion thereof between the throughbore and the outer surface of the body and extending axially between spaced annular grooves in the body so that when a suture is tied around the collar, the slits will allow the partially separated portions of the middle portion of the body between the slits to move relative to one another so that the middle portion can be tightly fixed or squeezed about a lead body of a pacing lead extending therethrough.

SUMMARY OF THE INVENTION

According to the invention there is provided a suture collar for use with a pacing lead body, said collar comprising a generally cylindrical body having opposite ends and having a throughbore therethrough for receiving a pacing lead body, said cylindrical body including a middle barrel portion and tapering end portions, each of which taper from the barrel portion to one of said ends, said barrel portion being separated from said tapering end portions by first and second suture receiving annular grooves, and said barrel portion having at least two generally longitudinally extending slits therein, each extending generally radially inwardly from the outer surface of said barrel portion to said throughbore to facilitate squeezing of the cylindrical body around a lead body when a suture is tied in one of said grooves.

Further according to the invention there is provided a method of securing a suture collar comprising a generally cylindrical body having opposte ends and having a throughbore therethrough for receiving a pacing lead body, said cylindrical body including a middle barrel portion and tapering end portions, each of which taper from the barrel portion to one of said ends, said barrel portion being separated from said tapering end portions by first and second suture receiving annular grooves, and said barrel portion having at least two generally longitudinally extending slits therein, each extending generally radially inwardly from the outer surface of said barrel portion to said throughbore to facilitate squeezing of the barrel portion around a lead body when a suture is tied in one of said grooves, said method including the steps of: sliding the suture collar on a lead body to the place of entry of the lead body into a vein after an electrode tip has been inserted into and properly located within a ventricle or atrium of a heart; tying sutures to the underlying tissue or the ligated vein in the area of the annular grooves; and then securing the sutures tightly around the collar in each groove so as to cause the cylindrical body to grip the lead body.

BRIEF DESCRIPTION OF THE DRAWINGS

FIG. 1 is a fragmentary view of the chest of a male showing in phantom the position of a pacing lead and pacer implanted in the male's chest.

FIG. 2 is a perspective view of the suture collar of the present invention surrounding a lead body of a pacing lead at its entry point into a vein.

FIG. 3 is a sectional view of the suture collar sutured to a vein as shown in FIG. 2 and is taken along line 3—3 of FIG. 2.

FIG. 4 is a perspective view of the suture collar of the present invention.

FIG. 5 is a side view of the suture collar of the present invention.

FIG. 6 is an axial sectional view of the suture collar and is taken along line 6'6 of FIG. 5.

FIG. 7 is a diametrical sectional view of the barrel portion of the suture collar and is taken along line 7—7 of FIG. 5.

FIG. 8 is a diametrical sectional view through a tapering end portion of the collar shown in FIG. 5 and is taken along line 8—8 of FIG. 5.

DESCRIPTION OF THE PREFERRED EMBODIMENT

Referring now to the drawings in greater detail there is illustrated in FIG. 1 the outline of the upper torso or chest of a human male 11 wherein there is shown in phantom a pacing lead body 12 extending between the heart 14 and a pacer 16 embedded in a pocket adjacent or under the shoulder of the male 11.

The lead body 12 of the pacing lead extends between an electrode (not shown) in the heart 14 and the pacer 16 for supplying electrical pulses to the electrode.

Also shown in FIG. 1 is a suture collar 20 constructed in accordance with the teachings of the present invention and situated on the lead body 12 as it enters a vein 22.

Referring now to FIG. 2 there is shown the suture collar 20 sutured by sutures 24 and 26 to the ligated vein 22 or tissue (not shown) surrounding same.

In accordance with the teachings of the present invention, the suture collar 20 is generally cylindrical in shape and has a central barrel portion 28 separated from tapering end portion 30 and 32 by annular grooves 34 and 36 in the collar 20 in which are received the sutures 24 and 26. Also in accordance with the teachings of the present invention, the barrel portion 28 has four equally radially spaced, i.e., at approximately 90°, and axially extending, slits 41, 42, 43 and 44 as best shown in FIGS. 3 and 7. These axial slits 41–44 extend radially inwardly from the outer cylindrical surface of the barrel portion 28 to a throughbore 46 extending through the suture collar 20 as shown in FIGS. 2, 6 and 7. Also, as shown in FIGS. 4, 5 and 6, these slits extend through the suture collar 20 in the area between the bottom 54 of the groove 34 to the throughbore 46 and from the bottom 56 of the groove 36 to the throughbore 46.

As best shown in FIGS. 5 and 6, the tapering end portions 30 and 32 taper from larger in diameter sections 60 and 62 having substantially the same diameter as the barrel portion 28 to a thinner sleeve end section 70 or 72.

As shown in FIG. 6, a central portion 76 of the throughbore 46 will be reduced in cross section or squeezed inwardly when a suture 24 or 26 is tied about the collar 20 in each of the grooves 30 and 32. In this respect, the four slits 41–44 permit quarter portions 81, 82, 83 and 84 (FIG. 7) in barrel portion 28 between the slots 41–44 to move inwardly so as to reduce the diameter of the portion 76 of the throughbore 46 through the barrel portion 28 when the sutures 24 and 26 are tied to squeeze the barrel portion sections 81–84 against the lead body 12. In this way, the suture collar 20 is tightly fixed onto the lead body 12 so that it is prevented from axial or longitudinal movement on the lead body 12 at its point of entry into the vein 22.

The slits 41–44 are very thin in thickness such that the adjacent barrel portion 20 quarter sections 81–84 are usually in slidable face to face contact with each other and the slits 41–44 are shown in the drawings as being larger in cross section only for the purpose of illustrating the invention disclosed herein.

The suture collar 20 is preferably made of a silicone elastomer material.

In use, and with reference to FIGS. 1, 2 and 3, an electrode tip (not shown) at the distal end of the pacing lead body 12 is inserted into the vein 22 and then into the heart 14. After the electrode tip has been suitable located in a ventricle or atrium of the heart 14 and the electrode tip fixed in place therein, the suture collar 20 is moved along the lead body 12 to the point of entry of the lead body 12 into the vein 22. Then, sutures 24 and 26 are secured in place within the underlying tissue (FIG. 3) or around a ligated vein 22. Then each of the sutures 24 and 26 is tied tightly around the suture collar 20 in the grooves 30 and 32 thereby to compress and squeeze the quarter sections 81–84 of the barrel portion 28 tightly against the lead body 12 so that the suture collar 20 is tightly secured to the lead body 12.

From the foregoing description it will be apparent that the suture collar of the present invention has a number of advantages, some of which have been described above and others of which are inherent in the invention. Also it will be apparent that modifications can be made to the suture collar 20 of the present invention without departing from the teachings of the present invention. Accordingly, the scope of the invention is only to be limited as necessitated by the accompanying claims.

I claim:

1. A suture collar for use with a pacing lead body, said collar comprising a generally cylindrical body having opposite ends and having a throughbore therethrough for receiving a pacing lead body, said cylindrical body including a middle barrel portion and tapering end portions, each of which taper from the barrel portion to one of said ends, said barrel portion being separated from said tapering end portions by first and second suture receiving annular grooves, and said barrel portion having at least two generally longitudinally extending slits therein, each extending generally radially inwardly from the outer surface of said barrel portion to said throughbore to facilitate squeezing of the cylindrical body around a lead body when a suture is tied in one of said grooves.

2. The suture collar of claim 1 wherein each one of said slits extends axially into the area between the bottom of each groove and said throughbore.

3. The suture collar of claim 1 wherein said barrel portion has four slits therein.

4. The suture collar of claim 3 wherein each of said slits extends axially into the area between the bottom of each of said grooves and said throughbore.

5. The suture collar of claim 4 wherein said slits ae approximately 90° apart around the barrel portion to form barrel portion quarter sections.

6. The suture collar of claim 1 being made of an elastomeric plastic material.

7. The suture collar of claim 6 wherein said suture collar is made of a silicone elastomer.

8. A method of securing a suture collar comprising a generally cylindrical body having opposite ends and having a throughbore therethrough for receiving a pacing lead body, said cylindrical body including a middle barrel portion and tapering end portions, each of which taper from the barrel portion to one of said ends, said barrel portion being separated from said tapering end portions by first and second suture receiving annular grooves, and said barrel portion having at least two generally longitudinally extending slits therein, each extending generally radially inwardly from the outer surface of said barrel portion to said throughbore to facilitate squeezing of the barrel portion around a lead body when a suture is tied in one of said grooves, said method including the steps of: sliding the suture collar on a lead body to the place of entry of the lead body into a vein after an electrode tip has been inserted into and properly located within a ventricle or atrium of a heart; tying sutures to the underlying tissue or the ligated vein in the area of the annular grooves; and then securing the sutures tightly around the collar in each groove so as to cause the cylindrical body to grip the lead body.

9. The suture collar of claim 1 wherein said slits are generally diametrically opposite each other.

10. The suture collar of claim 1 including three slits.

* * * * *